United States Patent [19]
Lingwood et al.

[11] Patent Number: 5,164,298
[45] Date of Patent: Nov. 17, 1992

[54] VEROCYTOTOXIN RECEPTOR ASSAY

[75] Inventors: Clifford A. Lingwood, Etobicoke; Mohammed A. Karmali, Willowdale; Magdy T. Basta, Scarborough, all of Canada

[73] Assignee: HSC Research Development Corporation, Toronto, Canada

[21] Appl. No.: 211,289

[22] Filed: Jun. 24, 1988

[51] Int. Cl.$^5$ ................. G01N 33/569; G01N 33/543
[52] U.S. Cl. .................................. 435/7.37; 435/7.92; 435/975; 436/501; 436/504; 436/518; 436/527; 436/528; 436/531; 436/534; 436/829
[58] Field of Search ................. 435/7, 810, 7.32, 7.37, 435/7.9, 7.92; 436/518, 519, 520, 533, 534, 808, 809, 810, 829

[56] References Cited

U.S. PATENT DOCUMENTS

| | | |
|---|---|---|
| 4,411,888 | 10/1983 | Klipstein et al. |
| 4,415,733 | 11/1983 | Tayot |
| 4,469,795 | 9/1984 | Ginns et al. |
| 4,476,119 | 10/1984 | della Valle et al. |
| 4,521,593 | 6/1985 | Martin |
| 4,723,205 | 2/1988 | Karlsson et al. |
| 4,863,852 | 9/1989 | Wilkins et al. ........................ 435/7 |

OTHER PUBLICATIONS

Cohen et al, "Roles of Globotriosyl- and Galabiosylceramide in Verotoxin Binding and High Affinity Interferon Receptor" J. Biol. Chem. 262(35) pp. 17088–17091 (Dec. 15, 1987).
Waddell et al, "Globotriosyl Ceramide is Specifically Recognized by the *Escherichia Coli* Verocytotoxin," Biochem. Biophys. Res. Com. 152(2) pp. 674–679 (Apr. 29, 1988).
Lindberg et al., Protein–Carbohydrate Interactions in Biological Systems, Lark D. ed., Academic Press pp. 439–446 London (1986).
Jacewicz et al., J. Exp. Med., vol. 163, pp. 1391–1401 (1986).
Huang et al., J. Bacteriol., vol. 166, pp. 375–379 (1986).
Lindberg, et al., J. Biol. Chem., vol. 262, pp. 1779–1785 (1986).
Lingwood et al., Can. J. Biochem. Cell Biol., vol. 63, pp. 1077–1085 (1985).
Lingwood et al, "Glycolipid Binding of Purified and Recombinant *Escherichia coli* Produced Verotoxin in vitro," J. Biol. Chem. 262(18) Jun. 25, 1987 pp. 8834–8839.
Cleary et al, "Shiga-Like Cytotoxin Production by Enteropathogenic *Escherichia coli* Serogroups," Infect. Immun. 47(1) pp. 335–337. Jan. 1985.
Lehtonen et al. "Antigen Attachment in ELISA." J. Immunol. Methods, 34(1980) pp. 61–70.

*Primary Examiner*—Esther L. Kepplinger
*Assistant Examiner*—Carol E. Bidwell
*Attorney, Agent, or Firm*—Banner, Birch, McKie & Beckett

[57] ABSTRACT

This invention relates to the identification of verocytotoxin receptors of the formula:

$$X-O-Y(R) \tag{I}$$

wherein Y is sphingosine, hydroxylated sphinogosine or saturated sphingosine,
wherein X is selected from said group and optionally a polysaccharide linking X to the —O—Y(R) group, and
wherein R is H, or a fatty acid and R is linked to the amine moiety of the sphingosine, in combination with an assay component and their use in novel receptor-binding assays for the detection and quantitation of verocytotoxins.

39 Claims, 8 Drawing Sheets

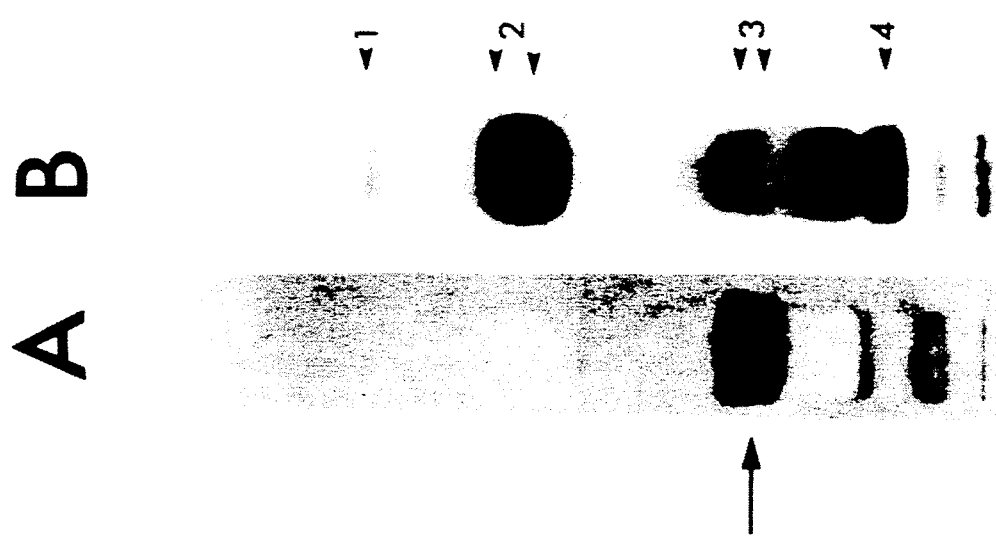
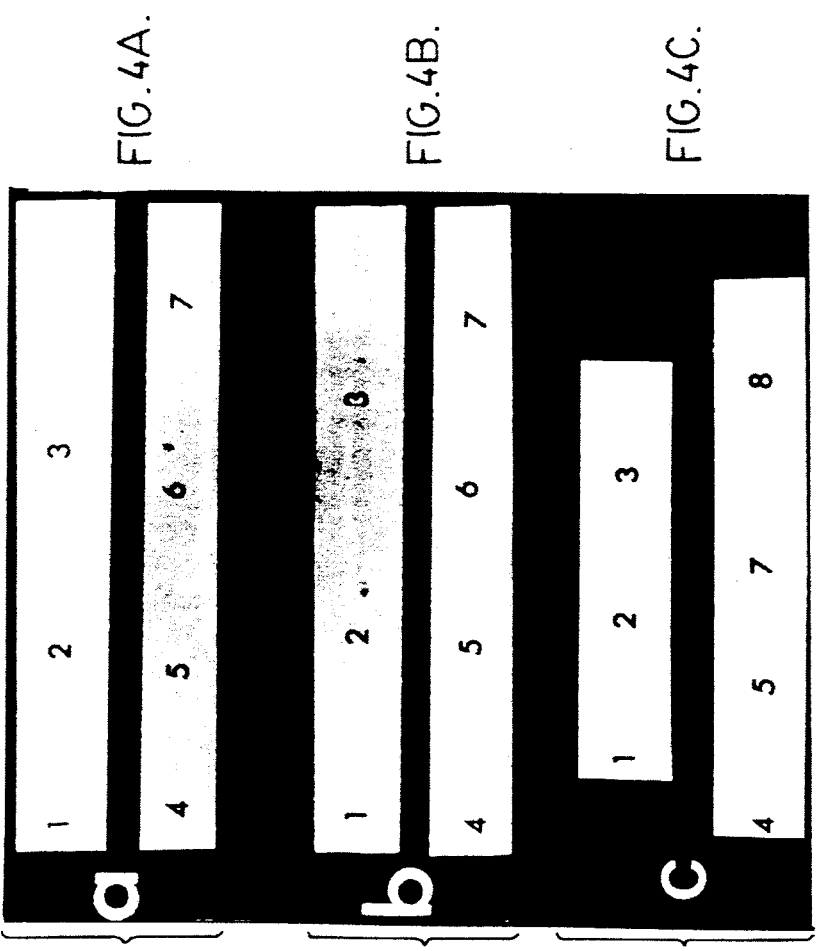

A  B a b c d e f g h i    a b c d e f g h i

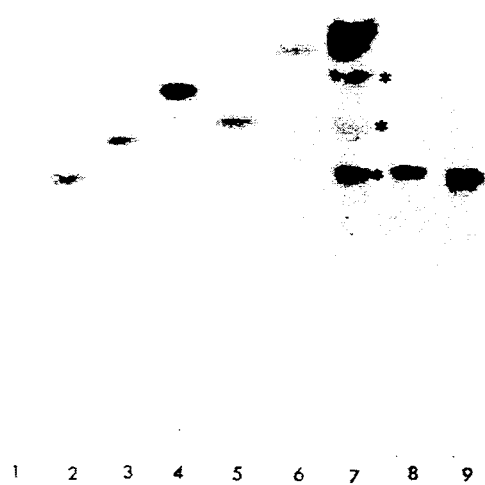
FIG.11C.
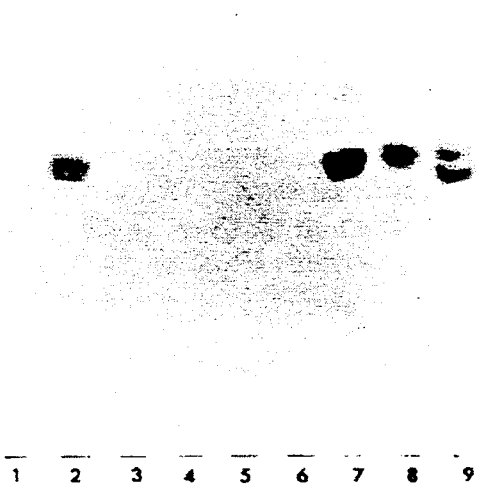
FIG.11D.
FIG.13A.
FIG.13B.

VEROCYTOTOXIN RECEPTOR ASSAY

FIELD OF THE INVENTION

This invention relates to the identification of the verocytotoxin receptor and its use in novel glycolipid binding assays.

BACKGROUND OF THE INVENTION

Verocytotoxin (VT) is an *Escherichia coli* produced toxin which has been shown to be involved in the aetiology of hemolytic uremic syndrome (HUS), the leading cause of pediatric renal failure. Some strains of *E. coli* elaborate cytotoxins that are active on cultured vero cells. At least two of the verocytotoxins, verocytotoxin 1 and verocytotoxin 2, are known to be produced by *E. coli* strains that are closely associated with a nonspecific diarrheal illness, as well as two distinct complications, the hemolytic uremic syndrome (HUS) and hemorrhagic colitis. A third verocytotoxin SLTII, distinct from VT2, has also been identified and other related cytotoxins are becoming recognized, but have yet to be fully characterized.

VT1 is closely related, both antigenically and biologically to Shiga Toxin produced by *Shigella dysenteriae* type 1 and is thus also referred to as Shiga-like toxin (SLT). It has been reported that the cytotoxin purified from *S. dysenteriae* type 1 binds to glycosphingolipids containing the Gal($\alpha$1-4)Gal sequence in a terminal position [Lindberg, A.A. et al (1986) in Protein Carbohydrate Interactions in Biological Systems, Lark D., ed. pp 439–446 *Academic Press*, London] although residual binding to globotetraosyl ceramide was observed. Keusch has recently confirmed that Shiga toxin binds specifically to Gb0se$_3$cer but maintains that this is a nonproductive binding in relation to cytotoxicity, since the addition of chiotriose protects against cytotoxicity with little effect on Gb0se$_3$cer binding [Jacewicz, M. et al, (1986) *J. Exp. Med.* 163 pp 1391-1404] although this result was not confirmed [Brown, J. E. et al, Annual Meeting of the American Society of Microbiologists, Las Vegas, Nev. Abstr. B107, p. 36]. Furthermore, there has yet been no discussion of the role of the lipid portions of these glycolipids in the receptor binding of either Shiga-toxin or verocytotoxin.

In *E. coli*, verocytotoxins are encoded by one or more bacteriophages and, furthermore, individual strains may produce either one or both VT1 and VT2. Both the natural and the recombinant forms of *E. coli* verocytotoxin have been isolated. One such recombinant cloned toxin is pJLB28 which expresses both the A and B subunits [Huang, A. et al. (1986) *J. Bacteriol.* 166, 375-379].

*E. coli* verocytotoxin has been characterized as having an "A" subunit of approximately 31,000 daltons and several "B" subunits each having an approximate molecular weight of 5,500 daltons. The A subunit possesses the biological activity of the toxin which is involved in inhibiting protein synthesis, whereas the B subunits are presumed to mediate specific binding and receptor-mediated uptake of the toxin.

At present, verocytotoxin is detected by a tedious and time consuming (but highly sensitive) procedure involving the determination of cytotoxicity to cells in culture. This procedure requires extensive cell culture facilities, the availability of toxin-neutralizing antibodies and thus considerable technical expertise. The assay is therefore performed in only a very few centers throughout the world. In fact, the assay is available only in reference and research laboratories. Moreover VTEC (verocytotoxin producing *E. coli*) may be a minor fraction of the intestinal flora and thus many colonies must be grown up and tested to exclude the possibility of these infections.

The demand for this assay is very high particularly in light of recent well publicized North American outbreaks in nursing homes, children's day care centers etc. Prospective studies in Alberta and Washington State have shown that VTEC are significant causes of endemic cases of hemorrhagic colitis and HUS. In Washington population based studies have shown that VTEC cause about 75% of sporadic cases of HUS. While *E. coli* 0157:H7 is the most common strain of VTEC, it is clear that HUS is caused by VTEC of many different serotypes. It has also become apparent that VTEC are a significant veterinary problem since they produce hemorrhagic colitis in calves. The oedema disease toxin which is produced by organisms found in pigs has also been shown to be a verocytotoxin and VTEC have been isolated from meat purchased at retail food outlets. Thus the need has also been strongly expressed for the screening of perishable food products for contamination with bacteria which produce this toxin. With improved assay technologies, such screening could be done at the place of manufacture.

Straightforward ELISA assays have so far not had the specificity or sensitivity required of such an assay. Part of the reason for this lies in the extreme biological potency of this toxin being effective at the picogram level.

SUMMARY OF THE INVENTION

In accordance with an aspect of the invention, a receptor assay system for the detection of the presence of verocytotoxin comprises a receptor which includes carbohydrate moieties selected from the group consisting of:

Gal($\alpha$1-4)Gal, Gal($\alpha$1-4)Gal($\beta$1-4)Glc,
GalNAc($\beta$1-3)Gal($\alpha$1-4)Gal($\beta$1-4)Glc,
GalNAc($\beta$1-3)Gal($\alpha$1-4)Gal, GalNAc($\beta$1-3)Gal and GalNAc.

In accordance with another aspect of the invention, the receptor in its preferred form is represented by the formula I:

$$X\text{---}O\text{---}Y(R) \qquad (I)$$

wherein Y is sphingosine, hydroxylated sphingosine or saturated sphingosine, wherein X is a carbohydrate moiety selected from the group consisting of:
Gal($\alpha$1-4)Gal, Gal($\alpha$1-4)Gal($\beta$1-4)Glc,
GalNac($\beta$1-3)Gal($\alpha$1-4)Gal ($\beta$1-4)Glc,
GalNac($\beta$1-3)Gal($\alpha$1-4)Gal, GalNac($\beta$1-3)Gal and GalNac, and optionally a polysaccharide linking X to the ---O---Y(R) group, and wherein R is H, or a chemical group non-inhibitory to receptor binding and R is linked to the amine moiety of the sphingosine, in combination with an assay component.

In accordance with another aspect of the invention a compound of formula I':

$$X\text{---}O\text{---}YH \qquad (I')$$

wherein Y is sphingosine, hydroxylated sphingosine or saturated sphingosine, wherein X is selected from the group consisting of Gal($\alpha$1-4)Gal, Gal($\alpha$1-4)Gal($\beta$1-4)Glc, GalNAc($\beta$1-3)Gal($\alpha$1-4)Gal($\beta$1-4)Glc, GalNAc($\beta$1-3)Gal($\alpha$1-4)Gal, GalNAc($\beta$1-3)Gal and GalNAc, and optionally a polysaccharide linking X to the —O—YH group.

In accordance with a further aspect of the invention, in a receptor assay for detecting the presence of verocytotoxin, the use of the receptor of formula I:

$$X-O-Y(R) \qquad (I)$$

wherein Y is sphingosine, hydroxylated sphingosine or saturated sphingosine, wherein X is selected from the group consisting of Gal($\alpha$1-4)Gal, Gal($\alpha$1-4)Gal($\beta$1-4)Glc, GalNAc($\beta$1-3)Gal($\alpha$1-4)Gal($\beta$1-4)Glc, GalNAc($\beta$1-3)Gal($\alpha$1-4)Gal, GalNAc($\beta$1-3)Gal and GalNAc, and optionally a polysaccharide linking X to the —O—Y(R) group, wherein R is H, or a chemical group non-inhibitory to receptor binding and R is linked to the amine moiety of the sphingosine.

Other and further advantages and features of the invention will be apparent to those skilled in the art from the following detailed description thereof, taken in conjunction with the accompanying drawings.

BRIEF DESCRIPTION OF THE DRAWINGS

FIG. 3 is a graph illustrating increased binding of natural verocytotoxin in correspondence with increasing concentrations of Gb0se3cer. No binding above background was observed for LacCer, Gb0se4cer, or DGDG.

FIGS. 4A, 4B and 4C are illustrations showing the binding of purified verocytotoxin from natural sources to glycolipids as visualized immunologically through the use of antiverocytotoxin antibodies.

FIGS. 5A and 5B are illustrations of verocytotoxin binding to vero cell glycolipids. The glycolipids of the vero cells have been separated by thin layer chromatography.

FIG. 6 illustrates the effect of $\alpha$-galactosidase on verocytotoxin glycolipid binding using glycolipids extracted from vero cells or Gb0se3cer standards as separated by thin layer chromatography and assayed for residual toxin binding using $^{125}$I-Protein A.

FIG. 9 is a chart showing the absorbance as measured at 490 nm for a series of *E. coli* culture supernatants including verocytotoxin producing *E. coli* demonstrating the specificity of the receptor-based ELISA assay.

FIG. 10 is a comparison between the VT levels measured by the traditional cytotoxic assay and the VT levels measured using the receptor-based ELISA on test samples from *E. coli* culture supernatants as isolated from ten different patients.

FIGS. 11A, 11B, 11C, and 11D show glycolipid binding of radioiodinated VT2 and unlabelled VT2.

FIG. 12 shows the VT2 cytotoxicity for Daudi cells.

FIGS. 13A and 13B show the VT2 binding to Daudi and VT1 resistant mutant cell glycolipids.

DETAILED DESCRIPTION OF THE PREFERRED EMBODIMENTS

In accordance with an aspect of this invention, one preferred embodiment of the verocytotoxin receptor is globotriosylceramide as illustrated in Formula I'':

$$\text{Gal}(\alpha 1\text{-}4)\text{Gal}(\beta 1\text{-}4)\text{Glc}-O-CH_2-\underset{H}{\overset{|}{C}}-\underset{OH}{\overset{|}{CH}}-CH= \cdots CH_3 \qquad (I'')$$

with NH*—C(=O)— chain to CH$_3$

*Deacylation site

There are three chemical groupings which combine to form the glycosphingolipid as illustrated (Formula I''): a carbohydrate chain, sphingosine and a fatty acid. In the findings detailed below, it is shown that the specificity of the verocytotoxin receptor is found in the carbohydrate chain and the sphingosine.

In accordance with one preferred embodiment of this invention, a carbohydrate chain having the terminal disaccharide Gal($\alpha$1-4)Gal($\beta$1-4) combined with sphingosine is a receptor for verocytotoxins 1 and 2. It is therefore appreciated that the P1 glycolipid would also be a receptor for verocytotoxin.

In accordance with another preferred embodiment of this invention, the carbohydrate chain GalNAc($\beta$1-3)Gal($\alpha$1-4)Gal($\beta$1-4)Glc combined with sphingosine is a receptor for pig oedema verocytotoxin.

It is appreciated that the sphingosine may be hydroxylated or saturated and that the length of the carbon chain may vary. It is also appreciated that the fatty acid chain may be of varying length and composition.

In accordance with another aspect of this invention, the glycosphingolipid may be deacylated thereby removing the fatty acid and a functional receptor for verocytotoxin remains. The deacylation site is indicated in Formula I''. As discussed below in further embodiments of the present invention, the combined carbohydrate and sphingolipid alone, without the fatty acid, is water soluble and therefore suitable for use in numerous receptor-based assays.

The receptor for verocytotoxin is identified and characterized in accordance with preferred embodiments of the invention. Furthermore, the use of this receptor in assays for the detection of the presence of verocytotoxins is demonstrated in accordance with the following preferred embodiments of the invention.

Figures 1A, 1B, 2A, 2B, 2C:
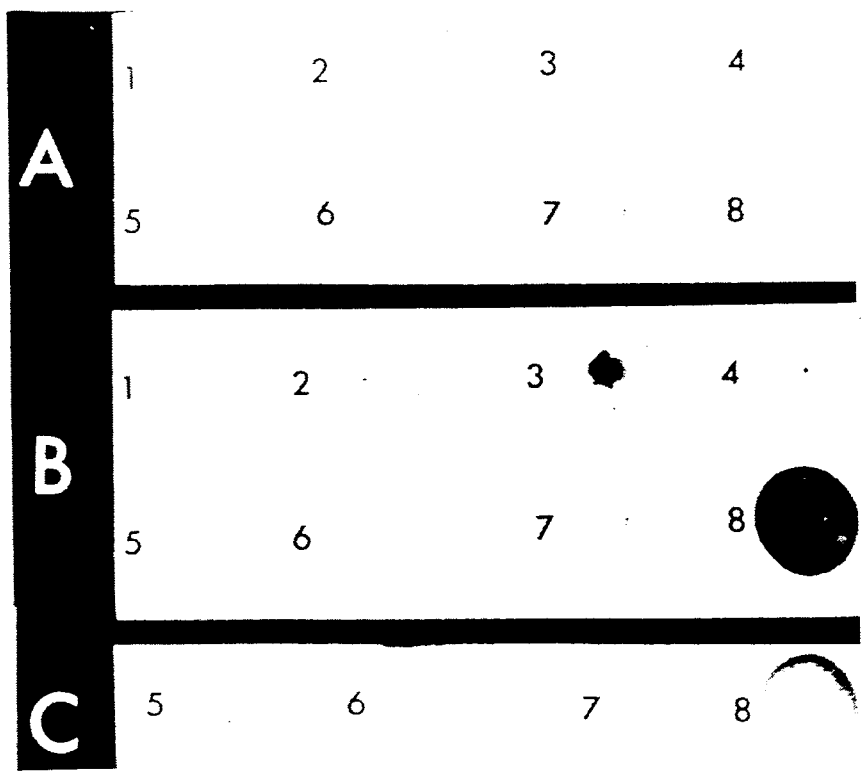
FIGS. 1A and 1B illustrate the specific binding of natural verocytotoxin to Gb0se3cer.
FIGS. 2A, 2B and 2C illustrate the glycolipid binding specificity for the cloned verocytotoxin pJLB28.

Purified natural verocytotoxin 1 was found to bind specifically to the glycosphingolipid globotriosyl ceramide (GbOse$_3$cer) [FIG. 1] and GbOse$_3$cer was identified as a receptor for verocytotoxin. Using thin layer chromatography purified glycolipids (5 nmol, FIG. 1A 2.5 nmol, FIG. 1B) were separated by tlc (chloroform/methanol/water, 60:25:4, v/w) and visualized by orcinol spray (FIG. 1A) or verocytotoxin binding, (FIG. 1B) using antiverocytotoxin and an immunoperoxidase conjugate as described in the followings Preparations and Examples. Lane 1, DGDG; lane 2, lactosyl ceramide; lane 3, GbOse$_3$cer; lane 4, GbOser$_4$cer.

No binding to lactosyl ceramide in which the terminal α-galactose residue is missing or globotetraosyl ceramide in which the terminal galactose is substituted in the 3 position with N-acetylgalactosamine was observed.

A similar glycolipid binding specificity was found for the cloned toxin pJLB28 expressing both the A and B subunits (FIG. 2). Culture supernatants of *E. coli* transformed with: FIG. 2A, pUC18 (containing no insert); FIG. 2B, pJLB28 (expressing A and B toxin subunits): FIG. 2C, purified verocytotoxin as used in FIG. 1 were assayed for glycolipid binding as in FIG. 2B. Glycolipids: 1. 3'-sulfogalactosyl ceramide; 2. galactosyl ceramide; 3. GbOse$_3$cer; 4. LacGer; 5. G$_{M2}$; 6. DGDG; 7. galactoglycerolipid; 8. GbOse$_3$cer. Specific binding to GbOse$_3$cer was observed. As with the purified toxin, recombinant verocytotoxin binding was greatly reduced for lactosyl ceramide and globotetraosyl ceramide, and substitution of glycerol for the sphingosine base resulted in the loss of binding. No background staining for the plasmid vector pUC18 carrying no insert was observed.

Figures 3, 12:
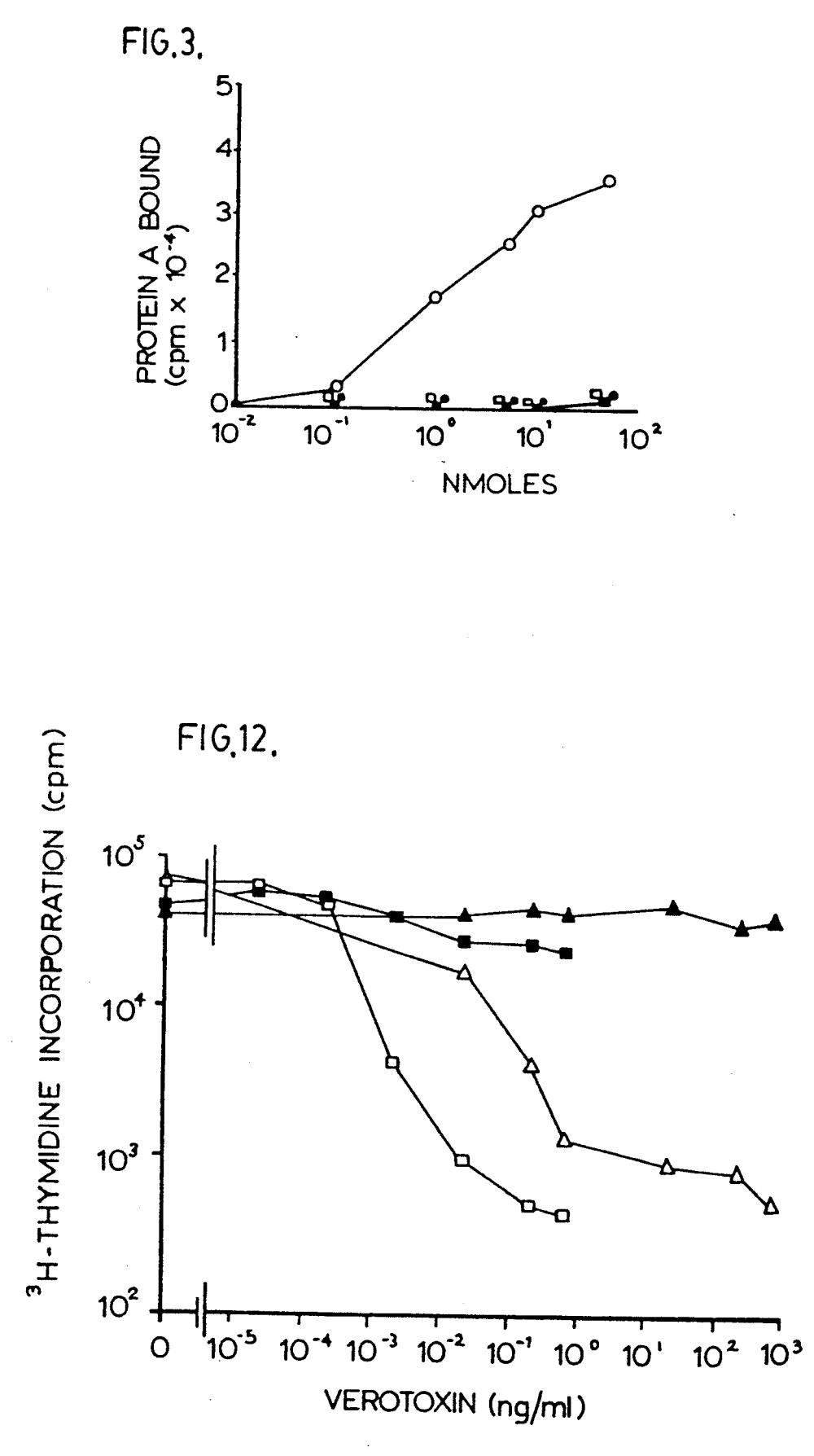

Thus, the verocytotoxin is strongly bound to GbOse$_3$cer, but substitution of the terminal αGal with GalNAc substituted in β1-3 linkage completely removes binding of the natural VT1 (FIGS. 1, 3 and 4) and vastly reduced the binding of the cloned VT1 species (FIG. 2). FIG. 3 shows the quantitation of glycolipid binding. In FIG. 3, increasing concentrations of glycolipid contained with 5 ul were dotted on the sheets. Toxin which bound was detected using $^{125}$I-labelled Protein A. Background values for binding without toxin have been substracted. Average of duplicates is shown. ○ GbOse$_3$cer □ DGDG ■ GbOser$_4$cer ● LacCer. In FIG. 4 binding of verocytotoxin to immobilized glycolipids was visualized immunologically. FIG. 4A control for background binding of polyclonal antitoxin in the verocytotoxin. FIG. 4B glycolipid dot bloc incubated with verocytotoxing visualized with polyclonal antitoxin. FIG. 4C glycolipid dot blot incubated with verocytotoxin visualized with monoclonal antitoxin. Background was as in FIG. 4A. Glycolipids: 2,3'-sulfogalactosyl ceramide. 2. galactosyl ceramide. 3. GbOser$_4$cer. 4G$^{M}{_2}$. 5. DGDG. 6. 3'-sulfogalalactosylgylcerolipid. 7. GbOser$_3$cer. 8. LacCer.

the sphingosine base of the glycolipid is also involved in the binding since digalactosyl diglyceride, containing the same terminal carbohydrate sequence as GbOse$_3$cer but linked to a glycero lipid moiety, rather than sphingosine, was also unreactive with the toxin. (FIGS. 3 and 4).

Binding curves were generated using $^{125}$I-Protein A (FIG. 3). No binding above background was observed for LacCer, GbOse$_4$cer, of DGDG at any concentration tested (0.01-50 nmol). However, binding to 0.1 nmol of GbOse$_3$cer could be detected. Similar results were obtained when toxin binding was detected using a polyclonal toxin-neutralizing antibody or a monoclonal antibody raised against the B subunit of verocytotoxing [FIG. 4]. These results suggest that both the lipid moiety and the terminal glycose moiety are involved in verocytotoxin-glycolipid binding.

Analysis of toxin binding to vero cell glycolipids shows that the natural toxin binds strongly to a species which migrates in the ceramide trihexoside region to tlc (FIG. 5). Metabolic labelling of glycolipids showed that this species was a relatively minor fraction of teh vero cell glycolipid content (FIG. 5). Neutral glycolipids of vero cells were metabolically labeled, extracted, and separated by tlc as described in the following Preparations and Example. Verocytotoxin binding to the separated glycolipids was determined as in FIG. 1. FIG 5.A, verocytotoxin binding, FIG. 5B, autoradiogram of labeled glycolipids; 1. galactosyl ceramide standard; 2. LacCer standard; 3. GbOse$_3$cer standard, 4. GbOser$_4$cer standard, Arrow in A indicates major toxin-binding species.

The specificity of verocytotoxin glycolipid binding was further confirmed by digestion of GbOse$_3$cer and vero cell glycolipids with α-galactosidase prior to tlc and assay of verocytotoxin binding. It was shown (FIG. 6) that removal of the terminal α-galactose residue deletes vertocytotoxin binding both to GbOse$_3$ce (now LacCer) and the vero cell glycolipids. Glycolipids extracted from vero cells of GbnOser$_3$cer standard were incubated with α-galactosidase as described in the following Preparations and Example, separated by tlc, and assayed for residual vercytotoxin binding using $^{125}$I-Protein A. Lanes A-J, autoradiogram showing verocytotoxin binding; Lanes K-L, glcolipids visualized by orcinol spray; Arrow GbOser$_3$cer standard (orcinol +ve). Vero cells glycolipids incubated in the absence (Lane A) and presence (Lane B) of α-galactosidase prior to assay. Increasing concentrations of GbOse$_3$cer incubated in the absence (Lanes C, E, G, and I) or presence (Lanes D, F, H, and J) of α-galactosidase (0.5 nmol, Lanes C and D; 1.0 nmol, Lanes E and F; 2.5 nmol, Lanes G, H, K and L; 5 nmol, Lanes I and J). The low level of residual vercytotoxin binding detected at higher glycolipid concentrations can be accounted for by residual undigested GbOse$_3$cer.

In accordance with one preferred embodiment of this invention, a novel glycosphingolipid binding assay for the detection of verocytotoxins has been developed. In one preferred embodiment the assay is based on the immobilization of deacylated globotriosyl ceramide in microtitre wells.

Globotrioxyl ceramide and other like glycosphingolipids are not water soluble and therefore would not be suitable for use in ELISA. However, in accordance with this invention, it has been shown that globotriosyl ceramide can be deacylated thereby rendering the glycosphinogolipid water soluble. In accordance with another aspect of this invention, it is shown that deacylation of the verocytotoxin receptor, globotriosyl ceramide, does not inhibit verocytotoxin binding.

In one preferred embodiment of this invention, deacylated globotriosyl ceramide is bound to a microtitre plate for use in an ELISA for the detection of verocytotoxin. The verocytotoxin present in verocytotoxin containing samples, or verocytotoxin positive controls will bind to the deacylated GbOse3cer which has been bound to the plate.

The glycolipid-bound toxin is visualized by use of a polyclonal rabbit antiserum and an immunoperoxidase indicator system. Other indicator systems well known to those skilled in the art of ELISA would also be suitable.

Figure 7:
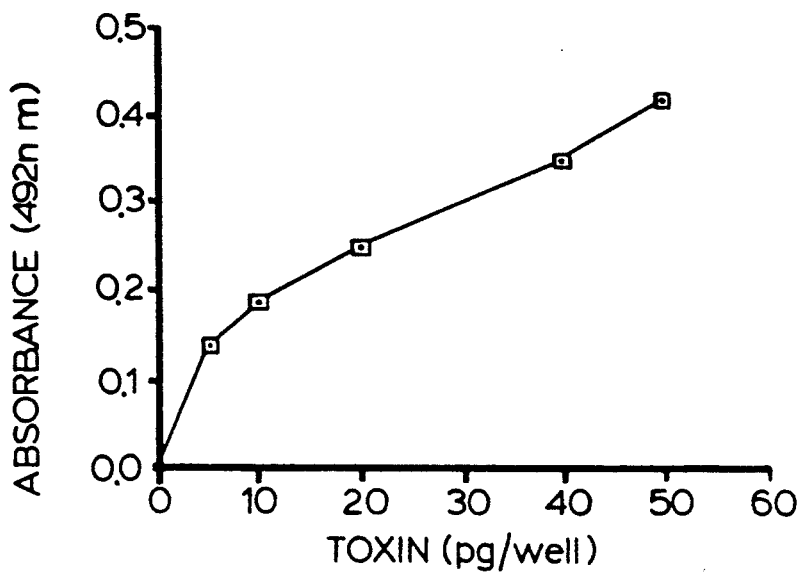
FIG. 7 illustrates the detection of VT1 toxin by receptor-based ELISA showing an increase in the absorbance at 492 nm corresponding to an increase in the quantity of VT1 toxin.
Figure 8:
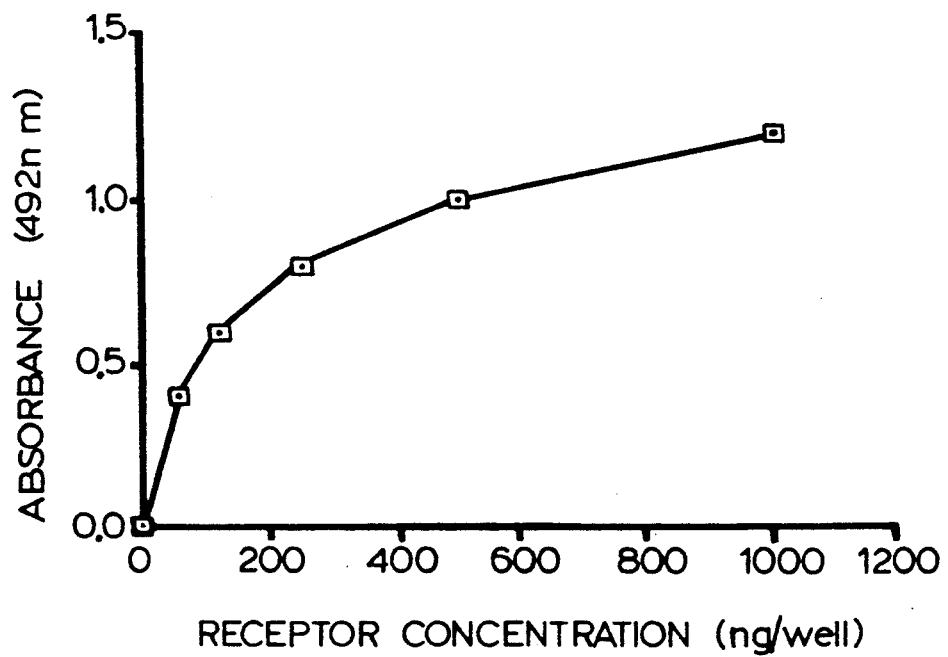
FIG. 8 is a plot depicting receptor concentration versus absorbance (492 nm) in a receptor-based ELISA at a constant concentration of VT1 toxin per well (200 pg).

The assay, as developed, can detect less than 5 pg of purified toxin (FIG. 7) and is dependent on the concentration of the immobilized deacylated receptor glycolipid concentration (FIG. 8). This level of detection is equivalent to the more complex cytotoxic assay presently available.

The specificity of thee receptor-based ELISA was tested against the culture supernatants of E. coli which produce the heat-labile enterotoxin or the heat-stable toxin, an enteroinvasive strain of E. coli and a non-toxigenic strain of by E. coli. As seen in FIG. 9, the only significant positive finding in the receptor-based ELISA was for E. coli strain producing verocytotoxin.

Culture supernatants of E. coli cultures isolated from ten different patients show a remarkable correlation between the verocytotoxin levels measured by the old cytotoxic assay and the novel ELISA receptor-based assay (FIG. 10). The advantage of the ELISA assay, or other similar plate-binding assays, is that it fulfills the clinical need for a quick, sensitive and specific test for verocytotoxin thereby allowing thorough epidemiological and veterinary screening for this toxin.

While the above detailed description embodies receptor-based ELISA incorporating deacylated GbOse3cer, a like assay could be performed using GbOse4. The selection of one of these glycolipids over the other would be dictated by the verocytotoxin which one wished to test for. If testing for VT1 or VT2, one would test using deacylated GbOse3cer. On the other hand if testing for the oedema disease toxin, one would use deacylated GbOse4cer. If one wanted to test for all verocytotoxin or for a cross-reactive verocytotoxin such as SLTII, then a mixture of the two modified glycolipids could be used.

Those skilled in the art of ELISA would also know that a deacylated glycolipid of formula I, having a free amino group, could also be covalently bound to another protein either directly or through the incorporation of a spacer arm. This second protein could then be used in the primary binding step in the assay. Similarly, instead of attaching the glycolipid to a protein as an assay component, it could be covalently bound directly to a solid phase support as an assay component or alternatively as set out in the subsequent examples, the assay component may be a liposome which contains the glycolipid receptor. Such solid phase supports include microtitre plates, test tubes, glass beads, nitrocellulose and latex particles. The plates or test tubes may be of glass or a plastic such as polyvinyl chloride, polystyrene or latex.

The principle of using the verocytotoxin receptor in a receptor-based assay for verocytotoxin could be applied to any of the well known assay technologies, including radioimmunoassay, cell-binding cytotoxicity assays, thin layer chromatography assays and agglutination assays. The principle could also be used in a fluorescence based receptor assay for verocytotoxin using toxin sensitive target cells as the receptor bearing vehicle.

Further details of the preferred embodiments of the invention will be understood from the following Preparations and Examples which are understood to be non-limiting with respect to the appended claims.

The Preparations and Examples detailed below incorporate materials identified and obtained as follows:

The glycolipids, galactosyl ceramide (kerosin), 3''-sulfogalacytosyl ceramide, and digalactosyl diglyceride (DGDG), were from Supelco. Lactosylceramide (LacCer), 3' sulfogalactosylglycerolipid, and galactogly cerolipid were prepared as previously described Lingwood, C. A. (1985) Biochem J, 231, 393–400. $G_{M2}$, GbOse3cer, and GbOse4cer were generous gifts from Dr. P. Strasberg, Division of Neurosciences and Dr. J. Clarke, Genetic Metabolic Program, The Hospital for Sick Children. All glycolipids gave a single sport on tlc (doublet for LacCer, GbOse3cer, GbOse4cer) when visualized with orcinol spray. [$^{14}$C] Serine and $^{125}$I-Chloro-1-naphthol was from Sigma, and goat antirabbit immunoglobulins conjugated to horseradish peroxidase were from Miles Laboratories, Plastic-backed Polygram SIL G tlc plates were purchased from Brinkmann Instruments (Ontario). Monoclonal antibody (Mab 13C4) against the B subunit of verocytotoxin was generously supplied by Dr. A. O'Brien (Uniformed Services University, Bethesda, Md.).

Preparation 1-Purification of Verocytotoxins

Verocytotoxin was purified from E. coli reference strain H.30 (0.26, K 60, H11) provided by J. Konowalchuk. The purification protocol used was a modification of the methods used by Petric, M. Karamali, M. A., Richardson, S., and Cheung, R. (1987) FEMS Microbiol. Lett. 41, 63–67 for purifying Shiga-like toxin (verocytotoxin) from the same reference strain and by Brown, J. E., Griffin, D. E., Rothman, S. W. and Doctor, B. P. (1982) Infect. Immun. 36, 996–1005, for purfiying Shiga toxin. Verocytotoxin containing a 31-kDa A subunit together with a B subunit of approximately 5 kDa was used in the binding studies at a titter of $10^4$ as measured in the vero cell cytotoxicity assay. Karmali, M. A., Petric, M., Lim, C., Fleming, P. C., Arbus, G. S., and Lior, H. (1985) J. Infect. Dis. 151, 775-782.

Preparation 2-Production of Antiverocytotoxin Antibodies

Adult male rabbits weighing approximately 2 kg were given an intravenous dose corresponding to 20 ng/kg body weight of purified verocytotoxin. This dose was equivalent to one-tenth of the 50% lethal dose (LD$_{50}$). The primary immunization was followed by 6 booster doses (at concentrations of 10–100 LD$_{50}$) given at 2-week intervals. The rabbits were bled prior to each immunizing dose, and the verocytotoxin-neutralizing antibody titer determineed by the method of Karmali, et al., (1985) J. Infect. Dis. 151, 775-782. The verocytotoxin-neutralizing antibody titer of the serum collected in the final bleed was 8192 while that of the perimmune serum was <2.

Preparation 3-Cloning of Verocytotoxin

A 1.7-kilobase fragment of the genome of a toxin converting bacteriophage H19B was cloned into a pUC18 in accordance with the method of Huang, A., DeGrandis, S., Friesen, J., Karmali, M., Petric, M., Corgi, R., and Brunton, J. (1986) J. Bacteriol 166, 375-379. E. coli TB1 which is nontoxigenic was transformed with the recombinant plasmid resulting in production of high levels of verocytotoxin activity. The E.

*coli* culture supernatant and a cytotoxin titer of $3 \times 10^4$ and was used as a source of cloned verocytotoxin. (pJLB28).

Preparation 4-Radiolabeling and Extracction of Vero Cell Glycolipids

Vero cells (No. 76, Americal Tissue Culture Collection, derived from the kidney of the green monkey) cultured, as previously described by Karmali et al. (1985), were grown for 75 h in the presence of [$^{14}$C] serine. Cells were removed with 1% trypsin. The cell pellet containing approximately $10^6$ cells was mixed with an equal number of unlabeled cells, washed 3 times with phosphate-buffered saline, extracted with 20 volumes of chloroform/methanol, 2:1 (v/v), and filtered through glass wool. The residue was partitioned against an equal volume of water. The lower phase was saponified in 1N NaOH in methanol at 37° C. overnight. Two volumes of chloroform and one volume of water were added, the lower phase was flash evaporated and lipids separated by tlc (chloroform/methanol/water, 65:25:4, by volume) without further purification. After toxin binding and immunostaining, radiolabeled lipids were detected by autoradiography. Nonlableled standards were visualized using orcinol spray.

Preparation 5-Digestion of Glycolipids with α-Galactosidase

Purified Globotriosyl ceramide (GbOse$_3$cer) and crude vero cell glycolipid extract were treated with α-galactosidase from coffee beans essentially as described by Bailly et al. Bailly, P., Piller, f., and Cartron, J. -P. (1986) *Biochem. Biophys. Res. Commun.* 141, 84–91. 5 nmol of GbOse$_3$cer and 500 μg of sodium taurocholate in chloroform/methanol were dried together and incubated in 50 mM citrate buffer, pH 4.5, containing 2 mM EDTA, 1% bovine serum albumin (w/v), and 1.0 unit of α-galactosidase at 37° C. for 24 h. Control samples were incubated in the absence of enzyme. Under these conditions greater than 90% of the GbOse$_3$cer standard was digested as judged by orcinol spray after tlc separation. The digested glycolipids were analyzed for verocytotoxin binding using $^{125}$-Protein A as described in Example 6.

EXAMPLE 1

Glycolipid Binding

Binding of verocytotoxin to purified glycolipids immobilized on thin layer chromatography (tlc) plates was performed essentially as previously described by Lingwood, C. A., et al., 1987*J. Biol. Chem.*, 262 8824–8839. Purified glycolipids (5 μl) were dot blotted on tlc plates. The tlc plate was then incubatec in 10 mM Tris ™ - saline, pH 7.4, containing 10% fetal bovine serum overnight at 4° C. The tlc blots were washed with Tris-saline and incubated overnight with verocytotoxin preparation. The blots were washed 5 times with Tris-saline and incubated overnight at 4° C. with 1% polyclonal rabbit antitoxin which had been previously treated with 0.8% formaldehyde as described in Lingwood, C. A. (1985) *Can. J. Biochem. Cell Biol.* 63, 1077–1085. (monoclonal antibodies were used at 1:10 dilution of hybridoma culture supernatant). The blots were washed 5 time with Tris-saline and further treated with peroxidase-conjugated goat anti-rabbit Ig for 2 h at room temperature (goat anti-mouse Ig peroxidase conjugate was used in the case of monoclonal antiverocytotoxin antibodies). Glycolipid-bound toxin was visualized after washing 5 times with Tris-saline by treatment of the blots with 4-chloro-1-naphthol peroxidase substrate Lingwood, C. A., (1985). The reaction was terminated by extensive washing with water. For quantitative analyses bound anti-verocytotoxin was detected by incubating with $^{125}$I-labelled Protein A (0.75 μCi/ml in phosphate-buffered saline) for 2 h at room temperature. The blots were washed extensively with saline, and bound Protein A was visualized by autoradiography. Glycolipid dots were cut out and counted in a gamma counter. Some batches of fetal bovine serum were found to give high background staining and eliminate specific verocytotoxin binding to glycolipids, possibly due to the presence of serum glycolipids. In other experiments 0.6% gelatin at room temperature was used to block nonspecific binding sites prior to verocytotoxin binding.

EXAMPLE 2

Preparation of Deacylated Globotriosyl Ceramide

Dry down the globotriosyl ceramide in a tube with a tight-fitting cap containing a teflon liner. It is advisable to begin the reaction with greater than 100 μg of globotriosyl ceramide. Yields of deacylated globotriosyl ceramide are potentially 60% so estimate the quantity of starting material accordingly.

Add 1000 μl of 1N NaOH in methanol. Cap the tube and place in a heating block at 100° C. Check the tube for leaks. The reaction should not boil.

Incubate the sample for 3.5 hours.

At the end of the incubation period acidify the reaction mixture to approximately pH 5 by adding 1N HCl. Check the pH with pH paper.

Dry the mixture quickly by rotorevaporation.

Add 2 mls of C/M 2:1 to the flask containing the residue of the reaction mixture and gently sonicate to disrupt the salt.

Filter the mixture through glass wool and collect the filtrate. Rinse the flask with $2 \times 1$ ml of C/M 2:1. Filter the rinses. Finally, wash the salt with 2 mls of C/M 2:1.

Perform a Folch extraction of the filtrate by adding 1.2 ml of H$_2$O and mixing well. Allow the mixture to partition and then separate the phases. Wash the lower phase $2 \times$ with 3 ml of previously prepared theoretical upper phase.

Dry down the combined upper phases and the washed lower phase and dissolve the remaining lipid in C/M 2:1.

Check the extent and quality of the preparation by thin layer chromatography followed by staining with orcinol and with ninhydrin.

EXAMPLE 3

Receptor-Based-ELISA for Detection of Presence of Verocytotoxin

I. Adsorption of deacylated globotriosyl ceramide

Deacylated globotriosyl ceramide was diluted to 10 μg/ml using PBS (pH 7.4). 100 μl of deacylated globotriosyl ceramide dilution was distributed into each well of a micro-ELISA plate. Two wells in the micro-ELISA plate were left empty as the substrate's control.

The micro-ELISA plate was covered and incubated for 16 hours at room temperature. The plate was washed three times by dispensing 300–400 μl of the PBS per well, waiting for 3 minutes before removing the washing solution each time. When the final wash solution was removed, it was made certain that no liquid remained in the wells.

II. Blocking

Each well of the micro-ELISA plate was filled with 110 μl of 2% BSA-PBS. The plate was covered and incubated for two hours at room temperature and then washed two times with PBS-0.05% polyoxyethylenesorbitan monolaurate (Tween 20 TM) using the same washing techniques indicated above.

III. Adding the Toxin

The samples, including standards and unknowns, were diluted using PBS-0.05% Tween to suitable concentrations for assaying. 100 μl was added into each well, except wells reserved for substrate control, using two wells for each dilution. The plate was covered and incubated for 16 hours at room temperature and then washed three times with PBS-0.05% Tween using the same washing techniques indicated above.

IV. Adding the Antibody

Rabbit anti-VT1 was diluted to the optimum dilution in PBS-0.05% Tween. 100 μl of the diluted serum was added to each well except those wells reserved for substrate control. The plate was covered and incubated for two hours at room temperature. The plate was washed three times with PBS-0.05% Tween using the same washing techniques indicated above.

V. Adding the Second Antibody (conjugates)

The conjugate (anti-rabbit IgG peroxidase) was diluted to its optimum dilution in PBS-0.05% Tween containing 2% BSA. Immediately after diluting of the conjugate, 100 μl of diluted conjugate was added to each well, except those wells reserved for substrate control. The plate was covered and incubated for 90 minutes at 37°. The plate was washed three times with PBS-0.05% Tween using the same washing techniques indicated above.

VI. Adding the Substrate 40 mg of orthophenylene diamine (OPD) was dissolved in phosphate-citrate buffer pH 5.0 and 150 μl of 300 g/l $H_2O_2$. The substrate solution must be prepared fresh immediately before use. 100 μl of substrate solution was distributed in all wells and the plate was incubated for 30 minutes in the dark at room temperature. 20 μl of 2M $H_2SO_4$ was added to bring the enzyme-substrate reaction to a stop. The optical density of each well was measured at 492 nm. The substrate control well containing only $H_2SO_4$ was used as the blank.

As noted, the receptor of this invention is capable of binding a variety of verocytotoxins. To further exemplify this position, the following Methods, Results and Discussion are provided with respect to binding the verocytotoxin VT2.

MATERIALS AND METHODS FOR VT2 INVESTIGATIONS

Toxin purification: A method for the purification of verocytotoxin to homogeneity has recently been developed as reported in Head S. et al (1987) International Symposium and Workshop on Verocytotoxin-producing Infections, Toronto abst. No. STF-16. VT2 was purified from an *E. coli* strain (E32511) producing no other cytotoxin, by ammonium sulfate precipitation, hydroxyapatite chromatography, chromatofocusing, Cibachron Blue chromatography and gel filtration. The purified toxin was radio-iodinated by the Bolton-Hunter reagent and contained radiolabeled species of apparent molecular weight 35 kDa (A subunit) and <14 Ka (B subunit). VT1 was purified as described Petric M. et al, (1987) *FEMS Microbiol. Lett.* 41 63–68.

Glycolipids: $Gb_3$ and $Gb_4$ of formula I were purified from human kidney. L C was from Biocarb (Sweden), GC and DGDG were from Supelco (Indiana), $GM_1$ was a generous gift of Dr. J. Callahan (Dept. Neurosciences HSC) and SGG and GG were prepared from bull testes as described in Lingwood, C. et al (1982) 262 8834–8839.

Glycolipid Binding: The binding of VT2 to glycolipids was assayed by means of a tlc overlay procedure previously noted in the prior Examples to demonstrate the binding specificity of VT1. Purified glycolipids (2.5 μg) were separated by tlc using Polygram SIL G plastic backed tlc plates (Brinkmann, Ontario). After separation, the plates were blocked in 0.3% gelatin at room temperature for three hours, washed with 100 mM Tris-saline pH 7.4 and incubated for two hours with purified $^{125}I$-VT2 (0.4 μg/ml) at 4° C. The plates were washed extensively and bound radiolabeled VT2 detected by autoradiography. Alternatively, in the case of unlabelled toxin samples, the bound toxin was visualized by treatment of the plates with specific rabbit anti VT2 serum followed by goat antirabbit immunoperoxidase conjugate and subsequent treatment with chloro-1-naphthol.

αGalactosidase digestion. Wild type Daudi cells and mutant VT20 cells were extracted with chloroform/methanol 2:1. The extracted glycolipids were tested for VT2 binding as above. $Gb_3$ and Daudi cell extracts were digested with αgalactosidase from coffee beans (Sigma, Mo.) as described by Bailly et al (1986) *Biochem. Biophys. Res. Commun.* 141 84–91 to remove the terminal galactose residue. Control digestions without enzyme were simultaneously performed. The effect on VT2 binding was then determined.

Cytotoxicity: Cytotoxicity in vitro was measured by assay of inhibition of Daudi cell DNA synthesis essentially as described in Cohen, A. et al (1987) *J. Biol. Chem.* 262, 17088–17091. Cells were cultured in the presence of toxin for 48 hours and pulsed with $^3H$-thymidine (1 μCi/ml) for four hours. Cells were then lysed by hypotonic shock, filtered, washed and the filtrate was counted in a scintillation spectrometer.

Adsorption of Cytotoxicity: Glycolipid liposomes were prepared containing 200 μg glycolipid together with cholesterol and lecithin in the ratio of 1:3:5 by weight. The lipids were mixed in organic solvent, dried together and sonicated in 0.5 ml phosphate buffered saline (PBS) and centrifuged for 2 mins at 8000 xg. The pellet was washed and resuspended in 0.5 ml toxin (tire $10^4$–$10^5$ CD units/ml) and incubated at 4° C. Aliquots were periodically removed, centrifuged and the supernatant assayed for residual cytotoxicity on cultured vero cells.

RESULTS ON VT2 INVESTIGATIONS

The glycolipid binding of VT2 is shown in FIGS. 11 A, C are glycolipids visualized by orcinol spray; FIGS. 11 B, D are VT2 bound to tlc separated glycolipids. Toxin binding was visualized in B) by autoradiography and using antitoxin for D) as described in the Methods. Glycolipids-lanes a: $Gb_4$, b: $Gb_3$, c: LC, d: gal cer., e: GMl, f: GG. g: DGDG; h: SGG, i: SGC., 1:$GB_4$, 2:$Gb_3$, 3:LC, 4:galcer., 5:DGDG. 6:GG, 7: Daudi cell lipids (*marks carbohydrate species), 8: $Gb_3$ from human erythrocytes, 9: $Gb_3$ from Fabry's kidney. It can be clearly seen that VT2 selectively binds to $Gb_3$ containing the terminal carbohydrate sequence galα1–4 gal. Although no binding was observed when this sequence was substituted with N-acetyl galactosamine in β1-3 linkage ($Gb_4$) or when the terminal galactose residue was missing (LC), it has been found by liposomal adsorption that at least minimal VT2 is capable of binding GB4. The substitution of glycerol for the sphingosine base (DGDG) also resulted in the loss of VT2 binding. Similar results were obtained for both iodinated (FIG. 12) and unlabelled (FIG. 13) VT2.

The Daudi human lymphoma cell line is highly sensitive to the cytotoxicity of VT1, and contains two VT1-binding glycolipids Gb$_3$ and galabiosyl ceramide (gala-1-4 gal). VT1 resistant mutant selected from these cells show a dramatic decrease in VT1 binding with a concomitant decrease in Gb$_3$ and galabiosyl ceramide content. The results in FIG. 12 show that wild type Daudi cells are also susceptible to VT2 cytotoxicity. Log-phase cells were grown in the presence of toxin for 48 hours and pulse labelled with $^3$H-thymidine to measure DNA synthesis. Open symbols-wild type Daudi cells, closed symbols-VT20 (VT1 resistant) Daudi cells. squares VT1; triangles VT2. The cells are about 100 fold less sensitive to VT2 than VT1 (FIG. 12). However, the Daudi mutant cells previously selected for resistance to VT1 are cross resistant to VT2 (FIG. 12) and the glycolipid extract from the resistant cells shows a marked reduction in VT2 binding Gb$_3$ and galabiosyl ceramide (FIG. 13). FIG. 13A-VT20 mutant cells (lane 1) and wild type Daudi cells (lane 2). Glycolipids from 10$^6$ cells were applied. FIG. 13B-effect of $\alpha$galactosidase. Glycolipids were digested overnight + (lanes 2,4)/-(lanes 1,3) $\alpha$galactosidase. Lanes 1, 2 Daudi cell extract; lanes 3, 4 Gb$_3$ standard. Digestion of Daudi cell glycolipids and standard Gb$_3$ with $\alpha$galactosidase resulted in the complete loss of VT2 binding (FIG. 13).

Figure 14A:
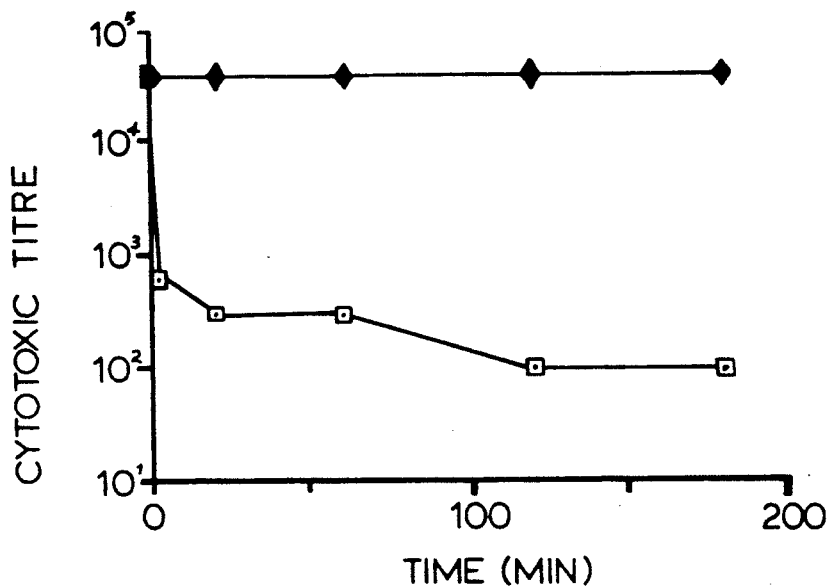
FIGS. 14A and B show the absorption of VT1 and VT2 cytotoxicity respectively, with Gb3 lyposomes and removal of binding after $\alpha$ galactosidase treatment.
Figure 14B:
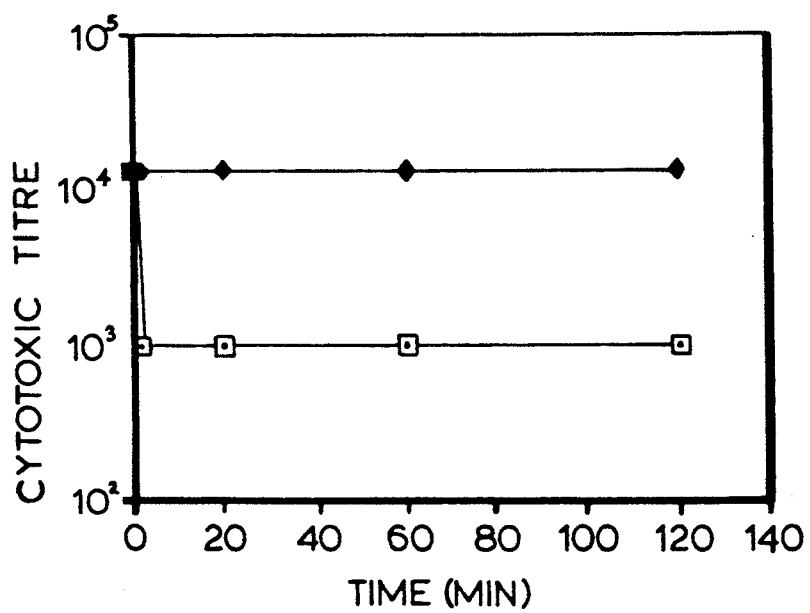

Phospholipid liposomes containing Gb$_3$ (but not DGDG) were highly efficient in removing the cytotoxicity in preparations of both VT1 and VT2 for vero cells in culture (FIG. 14). Toxin samples were treated with Gb$_3$ ( □—□ ) or DGDG ( ♦—♦ ) containing liposomes, aliquots removed at intervals, centrifuged and the supernatants assayed for residual cytotoxicity vero cells. FIG. 14A) is VT1 and FIG. 14B) is VT2. Greater than 95% of the VT1 and VT2 cytotoxicity was specifically removed within 2 mins incubation with Gb$_3$ liposomes at 4° C. The evidence that Gb$_3$ is the functional receptor for VT1 in vivo is positive. In addition, it appears that the pathogenesis of VT2 is mediated in a similar fashion.

Figures 6, 11A, 11B:
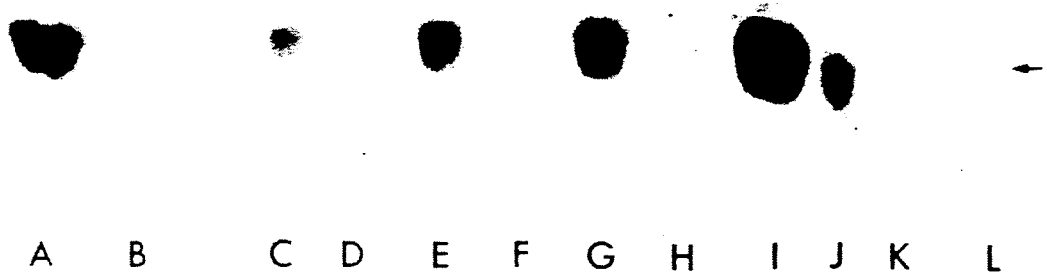

VT2 has been shown by nucleotide sequencing to be approximately 60% homologous to VT1. Our results show that the glycolipid specificity of VT1 and VT2 are virtually identical. Both toxins recognize the terminal $\alpha$Gal 1-4 Gal sequence of glycosphinogolipids, but do not bind to the same carbohydrate sequence of glycoglycerolipids (e.g. DGDG in FIG. 11). Gb$_3$ is recognized, whereas Gb$_4$, containing an additional N-acetyl galactosamine residue in $\beta$1-3 linkage does not bind. We have shown that both the iodinated VT2 (FIG. 11A) and the negative toxin (FIG. 11B) have the same glycolipid binding specificity. The sample of Gb$_4$ in FIGS. 11$a$ and 11$b$ was contaminated with Gb$_3$ which was then recognized by $^{125}$I-VT2 (FIG. 11B lane a). This sample was repurified before use in FIGS. 11C and 11D and binding was then no longer detected. No other toxin binding glycolipid was detected.

Daudi human lymphoma cells are highly susceptible to the cytotoxicity of VT1 and VT2 (FIG. 12). The reduced susceptibility to VT2 is in agreement with previous reports of reduced cytotoxicity for vero and HeLa cells in vitro. The VT1 resistant mutant cells (VT20) are cross resistant to VT2 (FIG. 12). VT2 binds to galabiosylceramide and to Gb$_3$ extracted from Daudi cells (FIG. 13A) and the binding is removed following digestion with $\alpha$galactosidase (FIG. 13B). Moreover, this binding is deleted for the glycolipid extract from VT1 resistant Daudi cells (FIG. 13B).

Thus VT1 and VT2 show the same glycolipid binding specificity in vitro. This accounts for their similar cytopathogenic selectivity in vitro (FIG. 12).

Our results with the selective absorption of VT2 cytotoxicity with Gb$_3$ liposomes (FIG. 14) confirms that $\alpha$galabiose coupled to BSA is able to protect HeLa cells from SLTII cytotoxicity as reported in Brown, J. E. et al, (1987) International Symposium and Workshop on Verocytotoxin-producing Infections, Toronto, Abst. no. STF-3.

Although preferred embodiments of the invention are described herein in detail, it will be understood by those skilled in the art that variations may be made thereto without departing from the spirit of the invention or the scope of the appended claims.

We claim:

1. A receptor assay kit for use in a receptor assay for the detection of the presence of verocytotoxin, said receptor assay kit comprising a receptor and a component for performing the specific binding assay, said receptor being represented by the formula I:

$$-X-O-Y \ (R) \qquad (I)$$

wherein Y is sphingosine, hydroxylated sphingosine or saturated sphingosine, wherein X is a carbohydrate moiety selected from the group consisting of:
Gal($\alpha$1-4)Gal, Gal($\alpha$1-4)Gal($\beta$1-4)Glc,
GalNAc($\beta$1-3)Gal($\alpha$1-4)Gal($\beta$1-4)Glc,
GalNAc($\beta$1-3)Gal($\alpha$1-4)Gal, GalNAc($\beta$1-3)Gal and GalNAc, and wherein
i) R is H, or a fatty acid,
ii) R is linked to the amine moiety of the sphingosine; and
iii) X is other than Gal($\alpha$1-4)Gal or Gal($\alpha$1-4)Gal($\beta$1-4)Glc when R is said fatty acid.

2. A receptor assay kit of claim 1 wherein R is H and X is Gal($\alpha$1-4)Gal($\beta$1-4)-Glc.

3. A receptor assay kit of claim 1 wherein R is said fatty acid and X is GalNAc($\beta$1-3)Gal($\alpha$1-4)Gal($\beta$1-4)Glc.

4. A receptor assay kit of claim 1 wherein said receptor is bound to a component for performing said assay selected from the group consisting of a microtitre plate, a test tube, glass beads, nitrocellulose, latex particles, proteins and liposomes.

5. A receptor assay kit of claim 1 wherein said component is the surface of a cell and said receptor is on the surface of said cell.

6. A receptor assay kit of claim 1, wherein said component is a liposome and said receptor is incorporated in said liposome.

7. The receptor assay kit of claim 1 wherein R is H.

8. The receptor assay kit of claim 7 wherein X is Gal($\alpha$1-4)Gal.

9. The receptor assay kit of claim 7 wherein X is GalNAc($\beta$1-3)Gal($\alpha$1-4)Gal($\beta$1-4)Glc.

10. The receptor assay kit of claim 1 wherein R, is a fatty acid.

11. The receptor assay kit of claim 10, wherein said fatty acid is represented by the formula:

$$\overset{O}{\underset{C}{\|}}\diagdown\!\diagup\!\diagdown\!\diagup\!\diagdown\!\diagup\!\diagdown\!\diagup\!\diagdown\!\diagup\!\diagdown\!\diagup\!\diagdown CH_3.$$

12. The receptor assay kit of claim 2, 3, 7, 8, 9, 10 or 11 wherein said component is a microtitre plate and said receptor is bound to wells of said plate.

13. The receptor assay kit of claim 2, 3, 7, 8, 9, 10 or 11 wherein said receptor is incorporated in a liposome which is bound to wells of a microtitre plate.

14. A receptor assay for detecting the presence of verocytotoxin in a specimen comprising the steps of:
contacting said specimen with a receptor for said verocytotoxin; and
assaying for binding of said verocytotoxin to said receptor, wherein said receptor is represented by formula I:

X—O—Y (R)  (I)

wherein Y is sphingosine, hydroxylated sphingosine or saturated sphingosine,
wherein X is a carbohydrate moiety selected from the group consisting of:
Gal($\alpha$1-4)Gal, Gal($\alpha$1-4)Gal($\beta$1-4)Glc, GalNac($\beta$1-3)Gal($\alpha$1-4)Gal($\beta$1-4)Glc, GalNac($\beta$1-3)Gal($\alpha$1-4)Gal, GalNac($\beta$1-3)Gal and GalNac,
wherein
i) R is H or a chemical group non-inhibitory to receptor binding,
ii) R is linked to the amine moiety of the sphingosine, and
iii) X is other than Gal($\alpha$1-4)Gal or Gal($\alpha$1-4)Gal($\beta$1-4)Glc when R is said fatty acid.

15. The assay of claim 14 wherein said fatty acid has the formula:

$$\overset{O}{\underset{C}{\|}}\diagdown\!\diagup\!\diagdown\!\diagup\!\diagdown\!\diagup\!\diagdown\!\diagup\!\diagdown\!\diagup\!\diagdown\!\diagup\!\diagdown CH_3.$$

16. The assay of claim 14 wherein the verocytotoxin is verocytotoxin 1 and wherein R is H and X is selected from the group consisting of Gal ($\alpha$1-4)Gal and Gal($\alpha$1-4)Gal($\beta$1-4)Glc.

17. The assay of claim 15 wherein the verocytotoxin is verocytotoxin 2.

18. The assay of claim 15 wherein the verocytotoxin is verocytotoxin 2 and wherein X is selected from the group consisting of GalNac($\beta$1-3)Gal($\alpha$1-4)Gal($\beta$1-4)Glc, GalNac($\beta$1-3)Gal($\alpha$1-4)Gal, GalNac($\beta$1-3)Gal and GalNAc.

19. The assay of claim 14 wherein the verocytotoxin is oedema disease toxin and X is selected from the group consisting of GalNac($\beta$1-3)Gal($\alpha$1-4)Gal-($\beta$1-4)Glc, GalNAc($\beta$1-3)Gal($\alpha$1-4)Gal, GalNAc($\beta$1-3)Gal and GalNAc.

20. The assay of claim 14 wherein the verocytotoxin is shig a like toxin.

21. The assay of claim 14 wherein said assay is selected from the group of assays consisting of ELISA assays, radioimmunoassays, thin layer chromatography assays, cytotoxicity assays and agglutination assays.

22. The assay of claim 21 wherein said receptor is adsorbed or bound to microtitre plates or test tubes.

23. The assay of claim 22 wherein said microtitre plates or test tubes are constructed of plastic.

24. The assay of claim 23 wherein said plastic is selected from the group of plastics consisting of polyvinyl chloride and polystyrene.

25. The assay of claim 21 wherein said receptor is covalently bound to microtiter plates, test tubes, glass beads or proteins.

26. The assay of claim 14 wherein said assay is a fluorescence based receptor assay for verocytotoxin.

27. An assay of claim 14, 18 or 19 wherein said X is linked to —O—Y (R) by a polysaccharide.

28. An assay of claim 16 wherein X is linked to —O—Y(R) by a polymer, polysaccharide or peptide.

29. An assay of claim 14 wherein R is H.

30. An assay of claim 29 wherein X is Gal($\alpha$1-4)Gal.

31. An assay of claim 29 wherein X is Gal($\alpha$1-4)Gal($\beta$1-4)Glc.

32. An assay of claim 29 wherein X is GalNAc($\beta$1-3)Gal($\alpha$1-4)Gal($\beta$1-4)Glc.

33. An assay of claim 14 wherein R, is a fatty acid.

34. A receptor assay of claim 29, 30, 31, 32 or 33, wherein said receptor is bound to wells of a microtitre plate.

35. A receptor assay of claim 29, 30, 31, 32, or 33, wherein said receptor is incorporated in a liposome bound to wells of a microtitre plate.

36. A microtitre plate for use in a receptor assay, said plate comprising at least one microtitre well having bound thereto a receptor represented by formula I:

X-O-Y (R)  (I)

wherein
Y is sphingosine, hydroxylated sphingosine or saturated sphingosine,
X is a carbohydrate moiety selected from the group consisting of:
Gal($\alpha$1-4)Gal, Gal($\alpha$1-4)Gal($\beta$1-4)Glc, GalNac($\beta$1-3)Gal($\alpha$1-4)Gal($\beta$1-4)Glc, GalNac($\beta$1-3)Gal($\alpha$1-4)Gal, GalNac($\beta$1-3)Gal and GalNac, and
wherein
i) R is H or a fatty acid;
ii) R is linked to the amine moiety of the sphingosine; and
iii) X is other than Gal($\alpha$1-4)Gal or Gal($\alpha$1-4)Gal($\beta$1-4)Glc when R is said fatty acid.

37. A microtitre plate of claim 36 wherein R is H and X is Gal($\alpha$1-4)Gal($\beta$1-4)-Glc.

38. A microtitre plate of claim 36 wherein R is said non-fatty acid and X is GalNac($\beta$1-3)Gal($\alpha$1-4)Gal($\beta$1-4)Glc.

39. A microtitre plate of claim 26, 37 or 38 wherein said receptor is incorporated in a liposome bound to said microtitre well.

* * * * *

UNITED STATES PATENT AND TRADEMARK OFFICE
CERTIFICATE OF CORRECTION

PATENT NO. : 5,164,298
DATED : November 17, 1992
INVENTOR(S) : Lingwood, et al.

It is certified that error appears in the above-identified patent and that said Letters Patent is hereby corrected as shown below:

IN THE CLAIMS

At column 14, line 29, please change the formula from "-X-O-Y(R)" to --X-O-Y(R)--, deleting the dash which appears before the X.

At column 15, lines 35 and 36, delete "chemical group non-inhibitory to receptor binding" and add --fatty acid--.

At column 16, line 2, delete "shig a like toxin" and add --Shiga-like toxin II--.

At column 16, line 62, delete "26", and add --36--.

Signed and Sealed this

First Day of March, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,164,298
DATED : November 17, 1992
INVENTOR(S) : Clifford A. Lingwood, et al It is certified that error appears in the above-identified that said Letters Patent is hereby corrected as shown below:

Column 16, line 60, delete "non-fatty" and add --fatty--.

Signed and Sealed this

Tenth Day of January, 1995

Attest:

BRUCE LEHMAN

*Attesting Officer*    *Commissioner of Patents and Trademarks*